United States Patent [19]

Wainwright

[11] Patent Number: 5,052,382
[45] Date of Patent: Oct. 1, 1991

[54] APPARATUS FOR THE CONTROLLED GENERATION AND ADMINISTRATION OF OZONE

[76] Inventor: Basil E. Wainwright, 80 Greenaleigh Rd., Yardley Wood, Birmingham, England, B14 4JE

[21] Appl. No.: 344,649

[22] Filed: Apr. 28, 1989
(Under 37 CFR 1.47)

[51] Int. Cl.[5] .................... A61M 15/02; A61M 37/00
[52] U.S. Cl. ...................... 128/202.25; 128/203.14; 128/204.21; 128/203.27; 422/186.19; 422/186.18; 604/25
[58] Field of Search .................... 128/202.25, 203.14, 128/204.21, 203.26, 203.27; 604/25; 422/186.18, 186.19, 186.2

[56] References Cited

U.S. PATENT DOCUMENTS

| | | | |
|---|---|---|---|
| 361,923 | 4/1887 | Brin | 128/202.25 |
| 743,432 | 11/1903 | Blackmarr et al. | 128/202.25 X |
| 854,965 | 5/1907 | Potter | 128/202.25 X |
| 909,309 | 1/1909 | Kölle | 128/202.25 X |
| 921,903 | 5/1909 | Smith | 128/202.25 X |
| 951,789 | 3/1910 | Ashley | 128/202.25 X |
| 983,907 | 2/1911 | Knips et al. | 128/202.25 X |
| 1,505,669 | 8/1924 | Quain | 128/202.25 X |
| 2,054,367 | 9/1936 | Fisch | 604/25 |
| 3,465,753 | 9/1969 | Levy et al. | 128/203.14 |
| 3,498,294 | 3/1970 | Zeff et al. | 128/203.14 X |
| 4,434,771 | 3/1984 | Slomnicki | 123/539 |
| 4,632,980 | 12/1986 | Zee et al. | 604/25 X |
| 4,778,456 | 10/1988 | Lokken | 604/290 |
| 4,877,588 | 10/1989 | Ditzler | 422/186.19 |
| 4,932,400 | 6/1990 | Persinger | 128/202.25 |
| 4,966,666 | 10/1990 | Waltonen | 204/164 |

FOREIGN PATENT DOCUMENTS

| | | | |
|---|---|---|---|
| 361134 | 4/1990 | European Pat. Off. | 128/203.12 |
| 1048879 | 1/1959 | Fed. Rep. of Germany | 604/25 |
| 3232716 | 3/1984 | Fed. Rep. of Germany | 604/25 |
| 171523 | 12/1934 | Switzerland | 604/25 |
| 246837 | 1/1947 | Switzerland | 604/25 |

OTHER PUBLICATIONS

P. 107 of Chemical Abstracts, Industrial Inorganis, 1976.

Primary Examiner—Edgar S. Burr
Assistant Examiner—Eric P. Raciti
Attorney, Agent, or Firm—Roylance, Abrams, Berdo & Goodman

[57] ABSTRACT

Apparatus (2) for the controlled generation and administration ozone, which apparatus (2) comprises a generator (4) for generating ozone, a monitor (6) for monitoring the ozone, a dosage device (8) for providing a correct amount of ozone for administration, and a computer control device (77) for controlling the operation of at least one of the generator (4), the monitor (6) and the dosage device (8).

9 Claims, 4 Drawing Sheets

APPARATUS FOR THE CONTROLLED GENERATION AND ADMINISTRATION OF OZONE

This invention relates to apparatus for the controlled generation and administration of ozone.

The treatment of patients with ozone is well known. The ozone can be used to treat viral and bacteriacidal infections and it is well known for ozone to be used in the treatment of a patient's blood and also to be used in the treatment of external sores and wounds. When a patient's blood is being treated, this blood is normally removed from the patient, treated and then recirculated to the patient. The beneficial effects of ozone may be applied to both human and animal patients.

Although the treatment of patients with ozone is well known and although the beneficial healing effects of ozone has been proved and well documented, problems often arise in the provision of suitable apparatus for the treatment of a patient with the ozone. Much of the existing apparatus involves outdated technology and the existing apparatus cannot easily and conveniently be used by medical personnel in the treatment of patients.

It is an aim of the present invention to obviate or reduce the above mentioned problem.

Accordingly, this invention provides apparatus for the controlled generation and administration of ozone, which apparatus comprises generator means for generating ozone, monitor means for monitoring the ozone, dosage means for providing a correct amount of ozone as a mixture of ozone and oxygen, and computer control means for controlling the operation of at least one of the generator means, the monitor means and the dosage means.

The apparatus of the present invention can be used in a simple and easy manner by medical personnel in the treatment of patients. The apparatus may form complete medical treatment centre in which substantially all the apparatus that could be required for various modes of application of the ozone is provided in one single simple to operate unit.

The monitor means may comprise a first monitor device for monitoring the ozone when it is generated by the generator means in order to ensure that a correct amount of ozone is generated, and a second monitor device for monitoring the ozone after use in order to determine how much of the ozone has been used whereby the apparatus is able to deliver the ozone in a required concentration for a required period of time in order to ensure that a treatment product or treatment area is properly treated. If desired, the monitor means may be provided in a feedback loop which enables an electrical input to the generator means to be reduced if too much ozone is being produced and which enables the electrical input to the generator means to be increased if an insufficient amount of ozone is being produced.

The generator means may comprise at least two cells. Each cell may have an electrode which is connected to at least one inverter. There may be three electrodes connected to three inverters. The or each inverter generates the power required for the ozone generation, for example high frequency, high voltage current. If desired, the generator means may comprise only one cell.

The generator means may comprise inner and outer tubes. The inner tube may be plated with gold on its inner surface. Other electrically conductive materials may be used. The inner and the outer tubes are preferably made from glass, usually a silica glass.

Preferably, the generator means includes cooling means for cooling the generator means during operations of the apparatus. The cooling means may be a corrugated insert.

When the generator means includes inner and outer tubes, the inner tube may contain the corrugated insert. The corrugated insert may extend the entire length of the inner tube. The corrugated insert may be made of copper or any other desired and appropriate material.

The outer tube may have three separate gold plated bands on its outer surface, with each band constituting an electrode for connecting to a separate inverter. More or less than three bands and electrically conducting materials other than gold may be employed. The outer tube may be surrounded by a corrugated sleeve, for example made of copper. The inner tube may then form a common electrode for the outer electrodes formed by the bands on the outer tube.

The inner and outer tubes may form an assembly which is dipped into a varnish which holds the various parts of the assembly together.

The cooling means may include a fan positioned at each end of the inner and outer tubes. One fan may operate in a push mode whilst the other fan operates in a pull mode. With such an arrangement, the insert in the inner tube helps the air from the fans to take any heat away.

The monitor means may monitor the amount of ozone generated by the generator means and/or administered.

Preferably, the monitor means comprises an ultra violet light source and a photocell detector. Other light sources and other light detectors may be used so that, for example, the photocell detector may be replaced by a strobed detector. The strobed detector may be strobed by a zeon light source.

Preferably, the dosage means is able automatically to provide the correct amount of ozone is dependence upon information fed to the dosage means. The dosage means may be able to control volume delivery of the ozone in relation to the ozone discharge time.

The apparatus of the present invention may include selector means for providing the generated ozone for a chosen one of a plurality of methods of administration. The selector means may comprise a valve unit for directing the ozone to at least one of blood purging apparatus for the treatment of a patient's blood, a constant flow container for large area external administration, and a cup device for small area external administration.

The apparatus of the invention may include pump means for enabling an operator to dial the volume of ozone to be delivered. The pump means may be a peristaltic pump or a twin piston valveless pump.

The apparatus of the invention may include ozone destructor means.

The apparatus of the invention may also include a purge device and blood container for use in the treatment of the patient's blood, a constant flow bag/boot for use in the large area external administration, and a cup device for use in the small area external administration.

Embodiments of the invention will now be described solely by way of example and with reference to the accompanying drawings in which.

Figure 1:
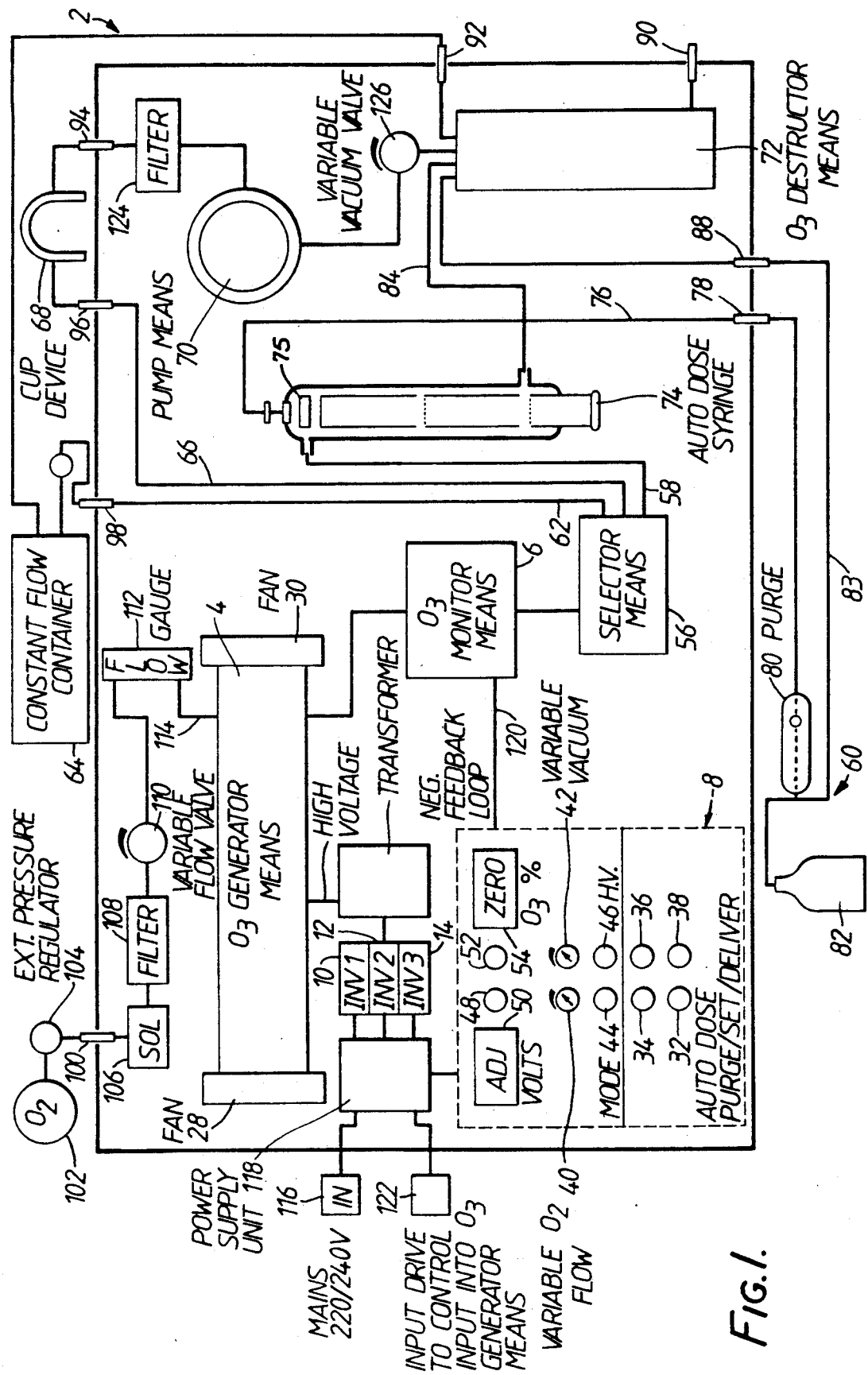
FIG. 1 shows a layout of first apparatus for the controlled generation and administration of ozone.

Referring to FIGS. 1 to 4, there is shown apparatus 2 for the controlled generation and administration of ozone. The apparatus 2 comprises generator means 4 for generating ozone, monitor means 6 for monitoring the amount of ozone generated by the generator means 4, and dosage means 8 for providing a correct amount of ozone for administration to a patient. The apparatus 2 further comprises computer control means which may be housed inside the dosage means 8 and which is for controlling the operation of the generator means 4, the monitor means 6 and the dosage means 8.

The generator means 4 has three separate cells and each of these cells is connected to three separate inverters 10,12,14 via a TFMR.

Figure 3:
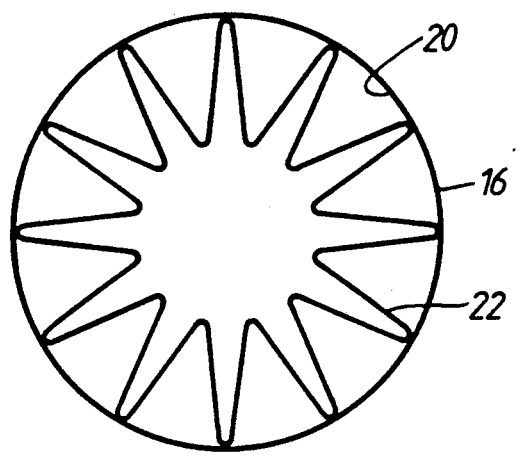
FIG. 3 is an end view of an inner tube forming part of generator means for generating ozone.
Figure 4:
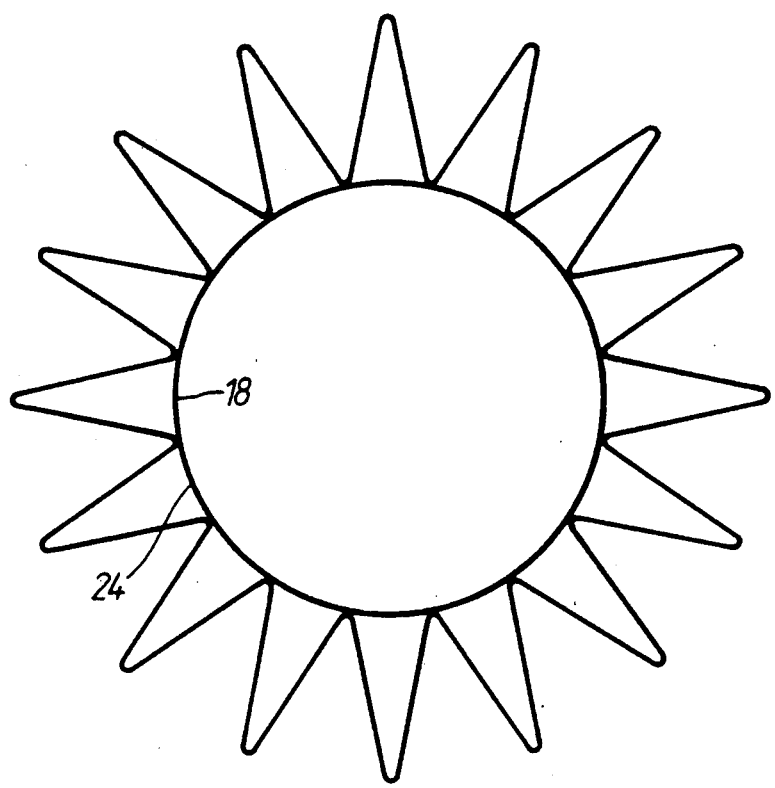
FIG. 4 is an end view of an outer tube forming part of the generator means for generating ozone.

As shown in FIGS. 3 and 4, the generator means 4 comprises an inner tube 16 and an outer tube 18. The inner tube 16 is plated with gold on its inner surface 20. The inner and the outer tubes 16,18 are made from silica glass. The inner tube 16 contains a corrugated insert 22 which is made of copper and which extends the entire length of the inner tube. The outer tube 18 has three separate gold plated bands (not shown) along its outer surface 24. Each of these bands constitutes one of the three electrodes for connection to one of the three inverters 10,12,14. The outer tube 18 is surrounded by a corrugated sleeve 26 which is made of copper. When the inner tube 16 is positioned inside the outer tube 18, the entire assembly is dipped into a varnish to hold the various parts of the assembly together. The assembly then has a common electrode form by the inner tube and three outer electrodes which are formed by the three gold plated bands and which are for connection to the three inverters 10,12,14.

As shown in FIG. 1, the generator means 4 is provided with a fan 28 at one end and with a fan 30 at the other end. The fan 28 operates in a push mode, whilst the fan 30 operates in a pull mode. Thus a good flow of air passes through the generator means 4 with the insert 22 helping to disperse the air and help the air to take away any heat that is generated. The copper of the insert 22 also makes electrical contact with the gold plating.

The monitor means 6 comprises an ultra violet light source (not shown) and a strobed detector (not shown). The detector is strobed by a zeon light source but it may be strobed by another light source if desired.

The dosage means 8 is able automatically to provide the correct amount of ozone in dependence upon information fed to the dosage means. The dosage means 8 controls the volume delivery in cubic centimetres in relation to the ozone discharge time. As can be seen from FIG. 1, the dosage means 8 has a button 32 for initiating an automatic dosage, a button 34 for initiating a purge sequence, a button 36 for initiating a set mode, and a button 38 for initiating a deliver mode. In addition, the dosage means 8 has a control knob 40 for varying oxygen flow, and a control knob 42 for varying the vacuum. Additionally, the dosage means 8 has a mode control knob 44 and a high voltage knob 46.

The dosage means 8 further has a control knob 48 for controlling volts required, these volts being shown in a panel 50. A similar control knob 52 enables the percentage of oxygen dialled to be shown in a panel 54.

The apparatus 2 includes selector means 56 for providing the generated ozone for a chosen one of a plurality of methods of administration. The selector means 56 comprises a valve unit for directing the ozone along conduit 58 to blood purging apparatus 60 for the treatment of a patient's blood, along conduit 62 to a constant flow container 64 for large area external administration, or along conduit 66 to a cup device 68 for small area external administration. The constant flow container 64 may be a bag or a boot.

The apparatus 2 includes pump means in the form of a peristaltic pump 70 which enables an operator to dial the volume of ozone to be delivered. The pump means is in effect a vacuum pump.

The apparatus 2 includes ozone destructor means 72.

When the apparatus 2 is used in the blood purging mode, then the ozone passes along conduit 58 to an automatically regulated dose syringe 74 which is connected by conduit 76 and a connector 78 to the purging apparatus 60. The purging apparatus 60 comprises a device 80 which receives oxygen and ozone from the syringe 74 via conduit 76 and connector 78. The oxygen and ozone pass through a flask 82 containing the blood to be treated with the ozone. Oxygen and ozone from the flask 82 are then recycled via line 83 and connector 88 to the destructor means 72. Oxygen is vented to atmosphere through an oxygen outlet 90. The syringe 74 is connected by a conduit 84 to the destructor means 72 so that excess ozone can be destroyed.

The apparatus 2 may be provided in a housing 26 provided with appropriate connectors 78, 92, 94, 96, 98, 100.

As shown in FIG. 1, an oxygen supply cylinder 102 is connected via an external pressure regulator 104 to the connector 100. Inside the housing 86, a solenoid 106 is connected to the connector 102. The oxygen can thus pass through the external regulator 104 and the solenoid 106 to a filter 108 and then to an internal variable flow valve 110. The variable flow valve 110 is connected as shown to a flow gauge 112 which connects by conduit 114 to the generator means 4. Thus the generator means 4 is controlably provided with oxygen for conversion into ozone.

The conversion of the oxygen into the ozone is via an appropriate electrical discharge to be effected between the inner tube 16 and the outer tube 18, and more specifically between the electrodes thereof. The discharge is preferably a plasma discharge. The discharge is provided via a mains input 116 which feeds a power supply unit 118 and which in turn feeds the inverters 10,12,14. The generated ozone is monitored by the monitor means 6 and the monitor means 6 is connected to the dosage means 8 by a negative feedback loop 120.

The housing 96 is also provided with an input drive 122 to control the input into the generator means 4.

The cup device 68 is connected to the pump means 70 by means of a filter 124. A variable vacuum valve 126 connects the pump means 70 to the destructor means 72.

During operation of the apparatus 2, the selector means 156 is able to divert the generated ozone for either one of the three available modes of use or, alternatively, to divert the apparatus into its negative feedback loop mode of use.

Figure 2:
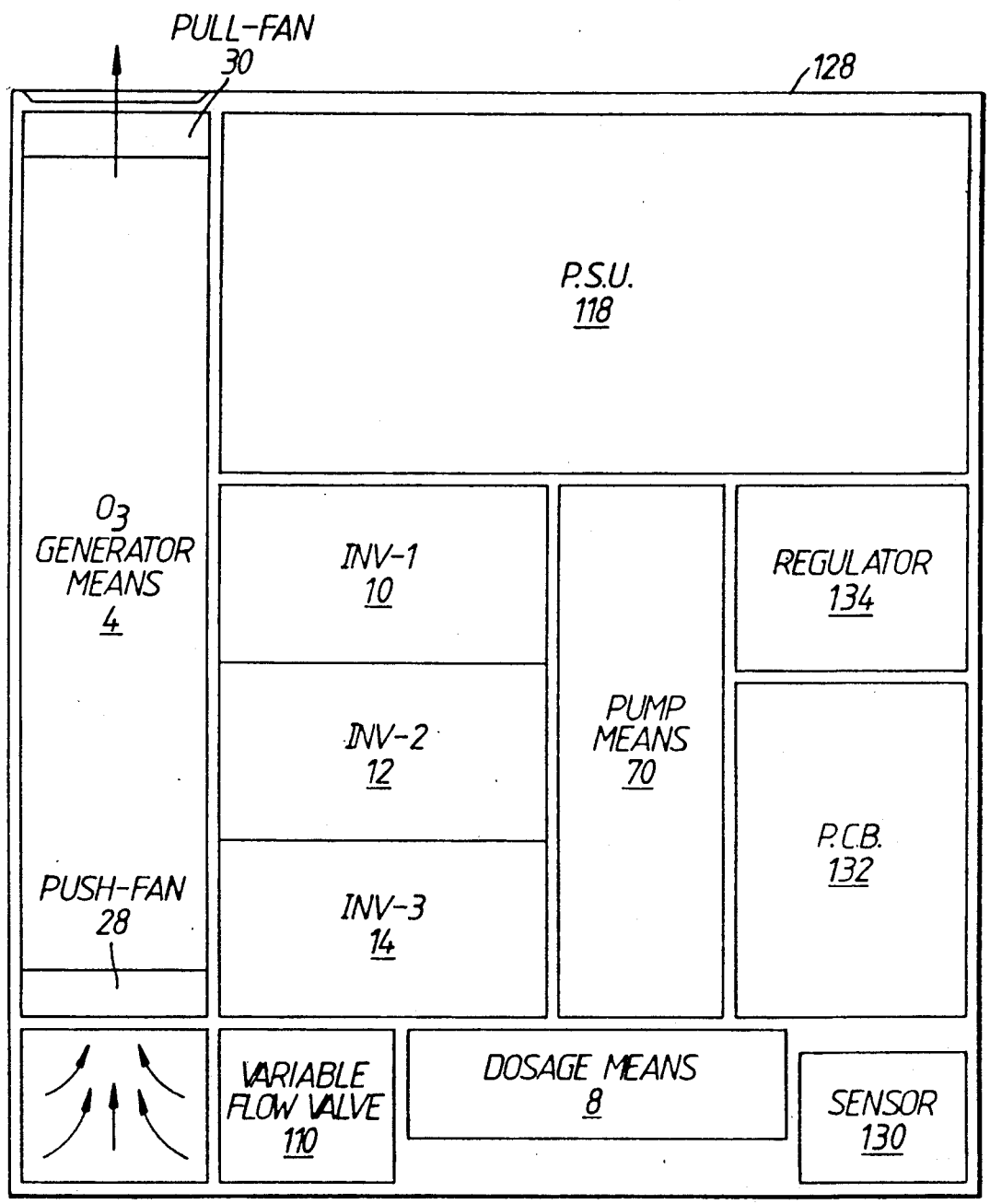
FIG. 2 shows how parts of the apparatus shown in FIG. 1 may be mounted on a base chassis.

Referring now to FIG. 2, there is shown how some of the components shown in FIG. 1 may be mounted on a base chassis 128. As shown in FIG. 2, the base chassis may be 600 mm long and 500 mm wide. The power supply unit 118 as shown in FIG. 2 may be variably driven by the input drive 122 (which is not shown in FIG. 2). FIG. 2 also shows positioned on the base chassis 128 a printed circuit board sensor 130 for use with the monitor means 6. Also shown is a printed circuit board 132 for use with a relay output, and a 15 volt regulator 134 for the power supply unit 118.

The computer control means may be effective to provide a hard copy readout of various operating perameters so that a physician does not have to rely solely on information shown on a screen.

The illustrated external pressure regulator 104 may be a regulating valve on the oxygen cylinder 102. The use of the extra regulator in the form of the solenoid 106 is to provide a safety feature in case the external pressure regulator 104 should become damaged during transit and supply to a hospital or medical treatment centre using the apparatus 2. The flow gauge 112 enables an operator to see what flow has been dialled on the variable flow valve 110. The flow gauge 112 may show a flow rate from 0-10 litres per minute.

The monitor means 6 preferably measures the concentration of ozone in micrograms per cubic centimetre in relation to the oxygen present. The use of the feedback loop 120 enables the electrical input to the apparatus 2 automatically to be reduced if the monitor means 6 senses that too much ozone is being produced. Similarly, if the monitor means 6 senses than an insufficient amount of ozone is being produced, then the electrical power input into the apparatus 2 can be appropriately increased to give the required amount of generated ozone. The apparatus 2 thus has in effect an ozone constant flow meter.

In addition to the uses of the apparatus 2 as a medical treatment centre, the apparatus 2 can also be used in other applications for which ozone is known to be useful, for example in the purification of water.

The ozone that is generated can be measured as a percentage by weight, a percentage by volume, or as is preferred, as micrograms per cubic centimetre. The use of pure silica glass tubes for the inner and outer tubes 16,18 is preferred since the apparatus 2 can then work at 185 nanometer wavelength of the ultra violet spectrum range. The silica tubes reflect the ultra violet wavelength back into the cells, thus reducing any spurious loss of the ultra violet light generated by the corona discharge occuring between the electrodes in the generator means 4. The generator means 4 is also chosen to be of a size that gives the correct and required type of ozone generation without degradation of the ozone occuring between 0 and 10 metres per minute of ozone generation.

The generator means 4 is also designed to minimise on any stalling of the oxygen and the ozone as they pass through the generator means 4, since this stalling will in itself result in a rapid degradation of the ozone.

Driving of the generator means 4 by the three separate inverters 10,12,14 gives very precise and controllable concentration yields of the ozone without overheating, and internal temperatures within the generator means 4 are able to be kept below 260° F. at high concentration yields of ozone of, for example, 115 micrograms per cc.

The apparatus 2 can be arranged to operate on 110 or 220 volts ac. The power supply unit 118 is effective to convert the alternating current from the mains to a variable 7-15 volts dc output.

During start up of the apparatus 2, the apparatus 2 will usually be completely purged to ensure that the apparatus 2 contains the ozone at the required concentration. This purging can be effected by an appropriate selection on the selector means 56.

Existing apparatus that is known to produce ozone for the treatment of patients tends to cause stalling of oxygen and ozone within the apparatus which is undesirable, for example in causing premature degradation of the ozone. Also, the known apparatus gives little or no control of the discharge of a sample from a syringe equivalent to the syringe 74. In the apparatus 2 of the present invention, the stalling of oxygen and ozone is substantially avoided and good control is achieved over the discharge of a sample from the syringe 74. The stalling of the oxygen and the ozone in the apparatus 2 of the present invention is avoided due to the fact that electrically operated drawing off means is employed. Similarly, the control of the discharge rates is achieved because the internal syringe 74 is driven by an electrical magnetic impulse motor in the form of a stepper motor 75. Because the stopper motor 75 will only operate on the number of pulses received, the stepper motor 75 is easily able to control the travel of charge and discharge of the syringe 74.

When the apparatus 2 is used employing the constant flow container 64, an infra red chopper sensor may be employed to calculate very accurately the amount of ozone delivered. Where it is desired to use the peristaltic pump means 70, the amount of the ozone to be delivered can be automatically dialled, for example in cubic centimetres. It will then only be necessary to press a start button and the delivery will commence at a desired flow rate and concentration. The discharge rate can be altered by varying the speed of the pump motor.

The destructor means 72 used in the apparatus 2 may be any ozone destructor means. Such ozone destructor means are already available.

During use of the apparatus 2, purging is preferably effected first with oxygen and then with the required concentration of the ozone.

The apparatus 2 can be made to be portable or static. In either mode of construction, the apparatus 2 can be simply used by medical personnel to provide in one medical treatment centre the facility to treat patients in a variety of ways.

Figure 5:
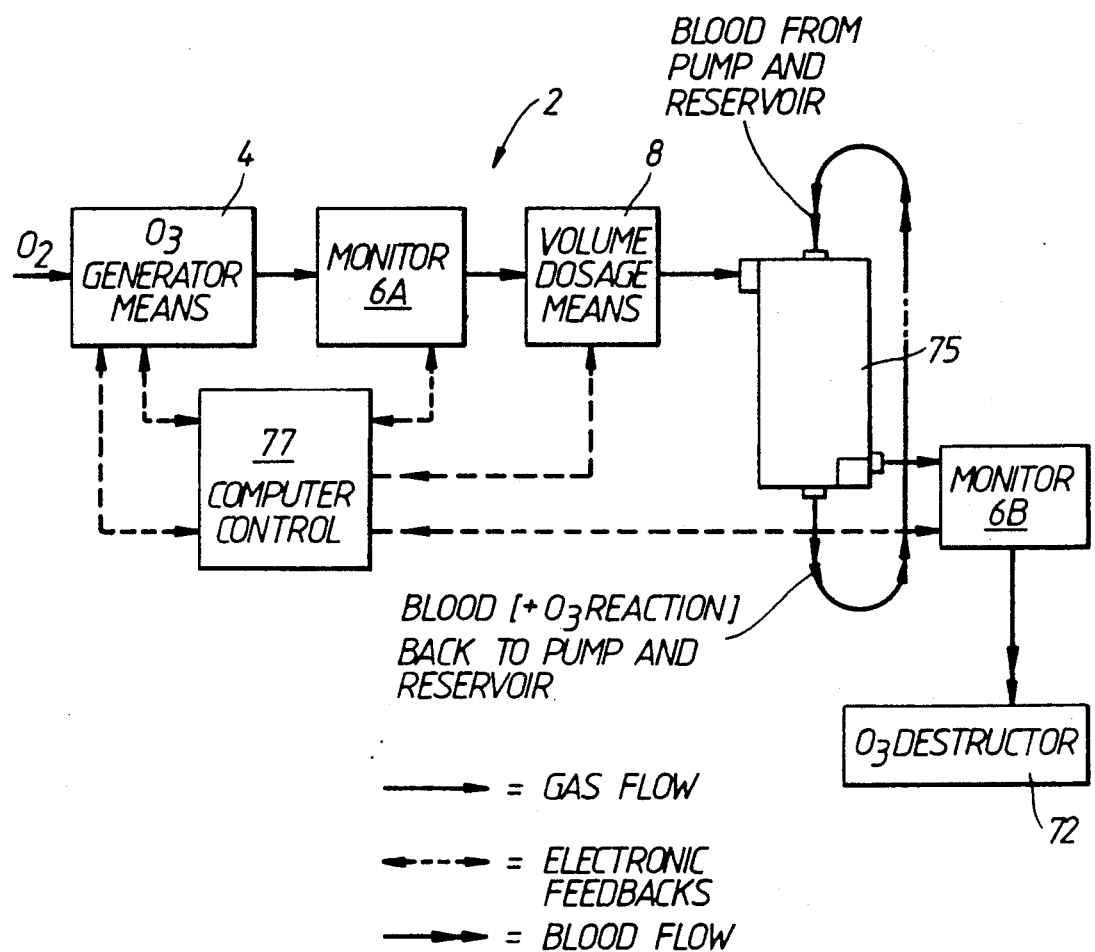
FIG. 5 shows second apparatus for the controlled generation and administration of ozone.

Referring now to FIG. 5, there is shown second apparatus for the controlled generation and administration of ozone. Similar parts as in the previous drawings have been given the same reference numbers for ease of comparison and understanding. In FIG. 5, there are two monitors, 6A and 6B. The monitors 6A and 6B in the apparatus 2 are in line. This means that the monitors 6A and 6B are such that the generated gas passes through the monitors as shown. The measured gas also passes into a hollow fibre device 75 as shown. The monitors measure the concentration of the ozone in the oxygen and ozone gas mixture constantly. The readout can be averaged over a short period of time to minimise readout fluctuations. Advantageously, the sensitivity of reading of the monitors is divided into two scales, being 0-10 μg per cc, and 10-100 μg per cc. The divisions on the first scale may be 0.1 μg. The divisions on the second scale may be 1.0 μg. Both readouts should be accurate to ±1% of true value.

The measurement of the ozone in the gas flow is computer linked via the computer control 77 to the generation of gas in order to ensure a constant level of production (concentration). The flow rate of the produced gas is variable from 0-5 litres per minute, adjustable by increments of 0.1 litres per minute.

The apparatus 2 is able to establish the maximum and minimum ozone production possible at the varying rates of gas flow. The apparatus 2 enables an operator to know the amount of ozone that is used in the treatment of blood or other product. This will be the amount prescribed by physicians. This amount is the difference between the gas delivered to the hollow fibre device 75 and the amount exhausted and is thus the value at monitor 6A minus the value at monitor 6B. The input monitor 6A and the exhaust monitor 6B are linked via the computer control 77 in real time to ensure a value of reactive gas used.

The ozone generator 4 is supplied with an initial source of oxygen for the generation of the ozone. Blood from a pump and a reservoir passes as shown to the hollow fibre device 75. Blood from the hollow fibre device with the ozone is circulated back to the pump and reservoir (not shown).

The ozone generator means 4, the monitor 6A, the monitor 6B, the volume dosage means 8, the computer control 77 and the destructor 72 form internal parts of the apparatus 2. The hollow fibre device 75 which is in fact a hollow fibre is used for transferring the gas to the substance such for example as blood to be exposed to chemical action. The hollow fibre device 75 may be replaced by any other suitable and appropriate device for transferring the oxygen and ozone mixture to the substance to be treated.

It is to be appreciated that the embodiments of the invention described above with reference to the accompanying drawings have been given by way of example only and that modifications may be effected. Thus, for example, the apparatus 2 can be designed differently, especially if it is to be used for the generation of ozone in the treatment of water or other products which do not involve the treatment of patients. Three different input sockets 116 may be provided for the operation of the apparatus 2 on 220 volts, 110 volts and 12 volts. The apparatus 2 can be arranged to operate on a.c. or d.c. from mains and/or battery as may be desired. The constant flow container 64, the cup device 68 and the gas injector device 80 are given as examples of the type of equipment that may be connected to the main body of the apparatus 2 of the invention. Thus a loop connection from the connector 78 and the device 80 could enable ozone to be drawn off into a hypodermic syringe.

Various different cell structures for the ozone generator means may be employed. The apparatus of the invention lends itself well to computerisation. The apparatus of the invention may be regarded as comprising generator means for generating ozone, in line monitor means, dosage means for giving for example volume control, and electronic integrated control means. The dosage means may be such as to dispense a volume of gas, for example on a time or pump basis. This is because an operator of the apparatus may need to know how much of the ozone is delivered in useable form for example how much of the ozone is taken up in a chemical reaction. After the gas (i.e. the oxygen with the required amount of ozone) has been dispensed by the dosage means, for example a dosimeter, then the gas is normally passed through a device for applying the gas to the required products, for example human blood. The monitor means may be positioned on the exhaust side of the device for applying the gas.

Because the correct amount of the ozone has been generated, this does not necessarily mean that the correct amount of the ozone will be used. It may therefore be desirable to measure the gas going in and the gas going out. The difference between the two measurements will give the amount of ozone being used. A single monitor may be used to measure the gas going in and the gas coming out. Alternatively two monitors may be used. The monitor or monitors may be linked to the computer means and the apparatus may be arranged to keep producing ozone until the required amount of ozone is used in the required chemical reaction. The apparatus may thus deliver ozone on a continuous basis until the difference between the gas going in and the gas coming out shows that the required amount of ozone has been taken up in the product being treated by the required predetermined amount.

The ozone may be produced on a continuous basis. The monitor means may be an absorption meter. One or two monitors may be used to measure the dose of the ozone absorbed, as opposed to measuring the flow of the ozone. If desired, the generator means for generating the ozone may comprise a single inverter. The single inverter may have three coils. Basically, each cell for the generator means may comprise an electrode and a dielectric for dispersing an electrical discharge.

The apparatus of the invention may be regarded as apparatus that produces a precise amount of ozone and oxygen and which forms an enclosed delivery system from the gas production to the gas use. The apparatus may be regarded as essentially comprising the generator means for generating the ozone, and the monitor means which may be an in line monitor that measures the concentration of the ozone in the mixture of air and ozone being produced. The apparatus may also include the dosage means which may be in the form of a dosimeter which delivers a fixed volume of a mixture of oxygen and ozone with the oxygen being a carrier gas for the ozone. Alternatively, the dosage means may be a syringe or a timer on a fixed flow device. The dosage means may also be means for allowing the mixture of oxygen and ozone to keep flowing until the apparatus calculates that the required or original amount of ozone has been used in the reaction. The mixture of the ozone and oxygen may flow into a reaction chamber which is external to the apparatus and which thus does not form a part of the apparatus. The mixture may flow in a constant flow mode, for a set time or as a predetermined volume of gas. Advantageously and preferably, the mixture of ozone and oxygen is continuously kept flowing until it is calculated that the required amount of ozone has been used in a desired reaction. The exhaust gases coming out of the reaction chamber may be taken back into a monitor which measures the ozone content of the exhaust gas. The apparatus may keep working until the original amount of ozone keyed in by an operator has been used in the reaction. The calculations required may be done by a micro-processor.

The product to be treated may be in the external chamber. The product to be treated with the required chemical reaction may be mammalian blood, other blood components and cell structures. The ozone may also be used to treat products other than blood so that the apparatus of the invention may be used to purify water with the ozone being passed through the water and being stopped, for example, when a certain predetermined keyed in amount of microgrammes of the ozone have been used up. Again, in the treatment of water, and other products such for example as the aging of wine, the sterilization of milk and the treatment of various other biologically active fluids, the mixture of oxygen and ozone gas entering and exhausting from the product is preferably measured with the difference between the measurements indicating the amount of ozone absorbed in the required reaction.

I claim:

1. Apparatus for the controlled generation and administration of ozone comprising:
   generator means for generating ozone gas;
   dosage means for mixing a predetermined amount of ozone with oxygen resulting in a predetermined concentration;
   monitor means for monitoring the generation and concentration of ozone;
   output means for dispensing the mixture of ozone and oxygen; and
   computer control means for delivering the mixture of ozone and oxygen for a predetermined period of time to the output means and for controlling the operation of at least one of the generator means, the monitor means and the dosage means;
   wherein said monitor means further comprises a first and a second detector means, said first detector means for monitoring the production of ozone by the generator means and the second detector means for monitoring a portion of the mixture of ozone and oxygen after administration in order to determine the quantity of ozone consumed during administration.

2. Apparatus according to claim 1 in which the generator means further comprises three separate drive inverters and at least two cells which each comprise inner and outer tubes, and in which a pair of cooling fans are positioned one at each end of the generator means for cooling the generator means by operating such that one of the fans pushes air through the generator means and the other one of the fans pulls air through the generator means.

3. Apparatus according to claim 1 wherein the output means is for treating a patient's blood, said output means comprising a dose discharge syringe means which is driven by a stepper motor for discharging controlled doses of a mixture of oxygen and ozone for the patient's blood, and a purge means for purging the blood treating means with the mixture of ozone and oxygen prior to treating the patient's blood.

4. Apparatus according to claim 3 wherein said output means further includes a cup device for treating small external treatment areas of a patient, a container for surrounding large external treatment areas of a patient, and a valve unit in selective fluid communication with the blood treating means, the cup device and the container.

5. Apparatus according to claim 1 and including a peristaltic pump for controlling delivery of ozone to the output means.

6. Apparatus according to claim 1 in which the monitor means further comprises an ultra violet light source and a photocell detector.

7. Apparatus according to claim 1 and including ozone destructor means.

8. Apparatus according to claim 1 and including a hollow fibre device for use in contacting the mixture of ozone and oxygen with the treatment product.

9. Apparatus for the controlled generation and administration of ozone comprising:
   generator means for generating ozone gas;
   dosage means for mixing a predetermined amount of ozone with oxygen resulting in a predetermined concentration;
   monitor means for monitoring the generation and concentration of ozone;
   output means for dispensing the mixture of ozone and oxygen; and
   computer control means for delivering the mixture of ozone and oxygen for a predetermined period of time to the output means and for controlling the operation of at least one of the generator means, the monitor means and the dosage means;
   wherein said computer control means further comprises a feedback loop means for reducing an electrical input to the generator means if more than the predetermined amount of ozone is being generated by the generator means, and for increasing an electrical input to the generator means if less than the predetermined amount of ozone is being generated by the generator means.

* * * * *